United States Patent [19]

Osborne et al.

[11] Patent Number: 5,690,642
[45] Date of Patent: Nov. 25, 1997

[54] RAPID EXCHANGE STENT DELIVERY BALLOON CATHETER

[75] Inventors: Thomas A. Osborne; Scott E. Eells, both of Bloomington, Ind.

[73] Assignee: Cook Incorporated, Bloomington, Ind.

[21] Appl. No.: 582,338

[22] Filed: Jan. 18, 1996

[51] Int. Cl.$^6$ .................................................. A61F 11/00

[52] U.S. Cl. ........................ 606/108; 606/198; 606/194; 606/195; 604/96

[58] Field of Search ..................................... 606/108, 194, 606/195, 192, 198; 609/96, 280; 128/772

[56] References Cited

U.S. PATENT DOCUMENTS

| | | |
|---|---|---|
| Re. 31,855 | 3/1985 | Osborne . |
| B1 Re. 31,855 | 8/1986 | Osborne . |
| D. 250,349 | 11/1978 | McFarlane . |
| 256,590 | 4/1882 | Pfarre . |
| D. 256,617 | 8/1980 | Clemens . |
| D. 272,651 | 2/1984 | Mahurkar . |
| 272,651 | 2/1883 | Coates . |
| 998,339 | 7/1911 | Hollins . |
| 1,060,665 | 5/1913 | Bell . |
| 1,290,647 | 1/1919 | Nyvall . |
| 2,175,726 | 10/1939 | Gebauer . |
| 2,269,593 | 1/1942 | Maltby et al. . |
| 2,474,665 | 6/1949 | Guarino . |
| 2,564,977 | 8/1951 | Hsi Hu . |
| 2,590,895 | 4/1952 | Scarpellino . |
| 2,625,932 | 1/1953 | Salisbury . |
| 2,657,691 | 11/1953 | Nordstrom, Jr. . |
| 2,687,131 | 8/1954 | Raiche . |
| 2,883,986 | 4/1959 | Luca et al. . |
| 2,936,760 | 5/1960 | Gants . |
| 3,053,257 | 9/1962 | Birtwell . |
| 3,225,762 | 12/1965 | Guttman . |
| 3,324,853 | 6/1967 | Czorny et al. . |

(List continued on next page.)

FOREIGN PATENT DOCUMENTS

| | | |
|---|---|---|
| 80520/87 | 10/1987 | Australia . |
| 10067/88 | 1/1988 | Australia . |
| 10074/88 | 1/1988 | Australia . |
| 43630/89 | 10/1989 | Australia . |
| 65741/90 | 10/1990 | Australia . |
| 70977/91 | 2/1991 | Australia . |
| 81971/91 | 7/1991 | Australia . |
| 35567/93 | 3/1993 | Australia . |
| 35568/93 | 3/1993 | Australia . |

(List continued on next page.)

OTHER PUBLICATIONS

Abele, John E.; "Technical Considerations: Physical Properties of Balloon Catheters, Inflation Devices, and Pressure Measurement Devices"; Transluminal Angioplasty, 1983; pp. 20–27.

Castaneda–Zuniga, Wilfrido R., et al.; "The Method of Transluminal Angioplasty"; Transluminal Angioplasty, 1983; pp. 3–10.

Castaneda–Zuniga, Wilfrido R., et al.; "The Mechanism of Transluminal Angioplasty"; Transluminal Angioplasty, 1983; pp. 11–19.

Creger, William P., Editor; "Percutaneous Transluminal Coronary Angioplasty"; Annual Review of Medicine; vol. 35, 1984, pp. 514–522.

(List continued on next page.)

Primary Examiner—Robert A. Hafer
Assistant Examiner—Justine R. Yu
Attorney, Agent, or Firm—Woodard, Emhardt, Naughton, Moriarty & McNett Patent and Trademark Attorneys

[57] ABSTRACT

A rapid exchange stent delivery balloon catheter which allows exchange from a balloon angioplasty catheter to a stent delivery catheter without the need to replace the angioplasty catheter wire guide with an exchange-length wire guide before exchanging the stent delivery catheter for the balloon angioplasty catheter. The stent delivery catheter of the present invention includes a relatively short wire guide shaft which is bonded to the catheter shaft only at a location distal to the inflation lumen.

14 Claims, 2 Drawing Sheets

U.S. PATENT DOCUMENTS

| | | |
|---|---|---|
| 3,435,826 | 4/1969 | Fogarty . |
| 3,463,152 | 8/1969 | Sorenson . |
| 3,467,101 | 9/1969 | Fogarty et al. . |
| 3,485,234 | 12/1969 | Stevens . |
| 3,550,591 | 12/1970 | MacGregpr . |
| 3,634,924 | 1/1972 | Blake et al. . |
| 3,687,138 | 8/1972 | Jarvik . |
| 3,731,692 | 5/1973 | Goodyear . |
| 3,757,768 | 9/1973 | Kline . |
| 3,766,924 | 10/1973 | Pidgeon . |
| 3,769,981 | 11/1973 | McWhorter . |
| 3,882,852 | 5/1975 | Sinnreich . |
| 3,989,255 | 11/1976 | Raffa . |
| 4,134,402 | 1/1979 | Mahurkar . |
| 4,149,535 | 4/1979 | Volder . |
| 4,195,637 | 4/1980 | Grüntzig et al. . |
| 4,198,981 | 4/1980 | Sinnreich . |
| 4,236,521 | 12/1980 | Lauterjung . |
| 4,244,362 | 1/1981 | Anderson . |
| 4,271,839 | 6/1981 | Fogarty et al. . |
| 4,289,128 | 9/1981 | Rüsch . |
| 4,299,226 | 11/1981 | Banka . |
| 4,307,722 | 12/1981 | Evans . |
| 4,323,071 | 4/1982 | Simpson et al. . |
| 4,367,747 | 1/1983 | Witzel . |
| 4,385,631 | 5/1983 | Uthmann . |
| 4,403,983 | 9/1983 | Edelman et al. . |
| 4,413,989 | 11/1983 | Schjeldahl et al. . |
| 4,419,067 | 12/1983 | Graafmann . |
| 4,439,186 | 3/1984 | Kuhl . |
| 4,451,252 | 5/1984 | Martin . |
| 4,468,224 | 8/1984 | Enzmann et al. . |
| 4,479,497 | 10/1984 | Fogarty et al. . |
| 4,490,421 | 12/1984 | Levy . |
| 4,526,175 | 7/1985 | Chin et al. . |
| 4,540,404 | 9/1985 | Wolvek . |
| 4,543,087 | 9/1985 | Sommercom et al. . |
| 4,545,390 | 10/1985 | Leary . |
| 4,552,554 | 11/1985 | Gould et al. . |
| 4,554,929 | 11/1985 | Samson et al. . |
| 4,561,439 | 12/1985 | Bishop et al. ............ 606/194 |
| 4,568,329 | 2/1986 | Mahurkar . |
| 4,571,240 | 2/1986 | Samson et al. . |
| 4,573,966 | 3/1986 | Weikl et al. . |
| 4,582,181 | 4/1986 | Samson . |
| 4,583,968 | 4/1986 | Mahurkar . |
| 4,585,000 | 4/1986 | Hershenson . |
| 4,597,755 | 7/1986 | Samson et al. . |
| 4,610,662 | 9/1986 | Weikl et al. . |
| 4,616,648 | 10/1986 | Simpson . |
| 4,619,643 | 10/1986 | Bai . |
| 4,630,609 | 12/1986 | Chin . |
| 4,636,272 | 1/1987 | Riggs . |
| 4,637,396 | 1/1987 | Cook . |
| 4,662,368 | 5/1987 | Hussein et al. . |
| 4,682,978 | 7/1987 | Martin . |
| 4,684,363 | 8/1987 | Ari et al. . |
| 4,687,469 | 8/1987 | Osypka . |
| 4,692,141 | 9/1987 | Mahurkar . |
| 4,702,252 | 10/1987 | Brooks et al. . |
| 4,744,366 | 5/1988 | Jang . |
| 4,748,982 | 6/1988 | Horzewski et al. . |
| 4,762,129 | 8/1988 | Bonzel . |
| 4,763,654 | 8/1988 | Jang . |
| 4,771,777 | 9/1988 | Horzewski et al. ............ 606/194 |
| 4,771,782 | 9/1988 | Millar . |
| 4,818,827 | 4/1989 | Ipcinski et al. . |
| 4,824,435 | 4/1989 | Giesy et al. . |
| 4,850,358 | 7/1989 | Millar . |
| 4,877,031 | 10/1989 | Conway et al. . |
| 4,892,519 | 1/1990 | Songer et al. . |
| 4,944,745 | 7/1990 | Sogard et al. . |
| 4,958,634 | 9/1990 | Jang . |
| 4,961,809 | 10/1990 | Martin . |
| 4,969,890 | 11/1990 | Sugita et al. . |
| 4,976,690 | 12/1990 | Solar et al. ............ 606/194 |
| 4,983,167 | 1/1991 | Sabota . |
| 4,990,139 | 2/1991 | Jang . |
| 5,040,548 | 8/1991 | Yock . |
| 5,041,126 | 8/1991 | Gianturco ............ 606/195 |
| 5,045,061 | 9/1991 | Seifert et al. . |
| 5,046,497 | 9/1991 | Millar . |
| 5,061,267 | 10/1991 | Zeiber . |
| 5,061,273 | 10/1991 | Yock . |
| 5,071,406 | 12/1991 | Jang . |
| 5,078,725 | 1/1992 | Enderle et al. . |
| 5,087,246 | 2/1992 | Smith . |
| 5,090,957 | 2/1992 | Moutafis et al. . |
| 5,102,390 | 4/1992 | Crittenden et al. . |
| 5,104,399 | 4/1992 | Lazarus . |
| 5,116,305 | 5/1992 | Milder et al. . |
| 5,135,484 | 8/1992 | Wright . |
| 5,135,487 | 8/1992 | Morrill et al. . |
| 5,135,535 | 8/1992 | Kramer . |
| 5,141,494 | 8/1992 | Danforth et al. . |
| 5,147,302 | 9/1992 | Euteneuer et al. . |
| 5,156,594 | 10/1992 | Keith . |
| 5,160,321 | 11/1992 | Sabota . |
| 5,180,367 | 1/1993 | Kontos et al. . |
| 5,195,955 | 3/1993 | Michael . |
| 5,205,822 | 4/1993 | Johnson et al. . |
| 5,209,729 | 5/1993 | Hofmann et al. . |
| 5,209,730 | 5/1993 | Sullivan . |
| 5,217,482 | 6/1993 | Keith . |
| 5,226,887 | 7/1993 | Farr et al. . |
| 5,232,445 | 8/1993 | Bonzel . |
| 5,232,446 | 8/1993 | Arney . |
| 5,257,974 | 11/1993 | Cox . |
| 5,261,879 | 11/1993 | Brill . |
| 5,263,932 | 11/1993 | Jang . |
| 5,269,793 | 12/1993 | Simpson . |
| 5,279,560 | 1/1994 | Morrill et al. . |
| 5,290,232 | 3/1994 | Johnson et al. . |
| 5,300,025 | 4/1994 | Wantink . |
| 5,304,132 | 4/1994 | Jang . |
| 5,306,247 | 4/1994 | Pfenninger . |
| 5,312,344 | 5/1994 | Grinfeld et al. . |
| 5,315,747 | 5/1994 | Solar . |
| 5,320,605 | 6/1994 | Sabota . |
| 5,324,269 | 6/1994 | Miraki . |
| 5,328,472 | 7/1994 | Steinke et al. . |
| 5,330,499 | 7/1994 | Kannesaka . |
| 5,336,184 | 8/1994 | Teirstein . |
| 5,338,300 | 8/1994 | Cox . |
| 5,342,297 | 8/1994 | Jang . |
| 5,344,413 | 9/1994 | Allman et al. . |
| 5,346,505 | 9/1994 | Leopold . |
| 5,364,357 | 11/1994 | Aase . |
| 5,368,567 | 11/1994 | Lee . |
| 5,370,616 | 12/1994 | Keith et al. . |
| 5,382,234 | 1/1995 | Cornelius et al. . |
| 5,382,261 | 1/1995 | Palmaz ............ 606/194 |
| 5,383,853 | 1/1995 | Jung et al. ............ 606/194 |
| 5,395,332 | 3/1995 | Ressemann et al. ............ 606/194 |
| 5,409,458 | 4/1995 | Khairkhahan et al. . |
| 5,413,557 | 5/1995 | Solar ............ 606/194 |
| 5,413,559 | 5/1995 | Sirhan et al. . |
| 5,456,694 | 10/1995 | Marin et al. ............ 606/198 |
| 5,458,613 | 10/1995 | Gharibadeh et al. . |
| 5,458,639 | 10/1995 | Tsukashima et al. . |
| 5,472,425 | 12/1995 | Teirstein . |
| 5,490,837 | 2/1996 | Biaeser et al. . |

| | | |
|---|---|---|
| 5,505,702 | 4/1996 | Arney. |
| 5,507,797 | 4/1996 | Suzuki et al. |
| 5,514,092 | 5/1996 | Forman et al. |
| 5,522,818 | 6/1996 | Keith et al. |
| 5,531,690 | 7/1996 | Solar. |
| 5,549,553 | 8/1996 | Ressemann et al. ............ 606/194 |
| 5,549,556 | 8/1996 | Ndondo-Lay et al. ........... 606/194 |
| 5,568,225 | 10/1996 | Teirstein. |

FOREIGN PATENT DOCUMENTS

| | | |
|---|---|---|
| A-50318/93 | 10/1993 | Australia. |
| A-16508/95 | 4/1995 | Australia. |
| 2146416 | 10/1920 | Canada. |
| 2060067 | 7/1929 | Canada. |
| 1092927 | 1/1981 | Canada. |
| 1284075 | 5/1991 | Canada. |
| 1309919 | 11/1992 | Canada. |
| 2091803 | 10/1993 | Canada. |
| 2109921 | 10/1993 | Canada. |
| 2109476 | 5/1994 | Canada. |
| 2126978 | 5/1994 | Canada. |
| 2113684 | 7/1994 | Canada. |
| 2166463 | 1/1995 | Canada. |
| 2170361 | 3/1995 | Canada. |
| 0 036 642 A2 | 3/1981 | European Pat. Off.. |
| 0 168 136 A1 | 5/1985 | European Pat. Off.. |
| 0 344 530 A1 | 5/1989 | European Pat. Off.. |
| 0 203 945 B1 | 8/1989 | European Pat. Off.. |
| 0 631 792 A1 | 12/1989 | European Pat. Off.. |
| 0 546 221 A1 | 11/1991 | European Pat. Off.. |
| 0 274 129 B1 | of 1992 | European Pat. Off.. |
| 0 348 692 B1 | 5/1992 | European Pat. Off.. |
| 0 513 818 A1 | 5/1992 | European Pat. Off.. |
| 0 515 119 A1 | 5/1992 | European Pat. Off.. |
| 0 517 654 A2 | 5/1992 | European Pat. Off.. |
| 0 564 894 A1 | 3/1993 | European Pat. Off.. |
| 0 309 754 B1 | 7/1993 | European Pat. Off.. |
| 0 279 959 B1 | 8/1993 | European Pat. Off.. |
| 0 397 357 B1 | 9/1993 | European Pat. Off.. |
| 0 595 308 A1 | 10/1993 | European Pat. Off.. |
| 0 623 360 A1 | 4/1994 | European Pat. Off.. |
| 0 380 873 B1 | 5/1994 | European Pat. Off.. |
| 0 362 268 B1 | 12/1994 | European Pat. Off.. |
| 329354 | 2/1903 | France. |
| 591963 | 7/1925 | France. |
| 592193 | 7/1925 | France. |
| 821344 | 12/1937 | France. |
| 19346 | 9/1882 | Germany. |
| 867144 | 2/1953 | Germany. |
| 2259865 | 6/1974 | Germany. |
| 28 28 447 | 9/1979 | Germany. |
| 29 18 282 | 11/1980 | Germany. |
| 30 28 089 | 2/1981 | Germany. |
| 29 34 628 A1 | 3/1981 | Germany. |
| 31 07 392 A1 | 9/1982 | Germany. |
| 32 35 974 A1 | 6/1983 | Germany. |
| 34 04 661 C1 | 9/1985 | Germany. |
| 34 06 294 A1 | 9/1985 | Germany. |
| 34 42 736 A1 | 5/1986 | Germany. |
| 35 38 739 A1 | 7/1987 | Germany. |
| 39 38 727 A1 | 10/1990 | Germany. |
| 42 00 030 A1 | 7/1993 | Germany. |
| 55-88771 | 4/1980 | Japan. |
| 84-253339/41 | 2/1983 | Japan. |
| 2-63474 | 3/1990 | Japan. |
| 4-35446 | 3/1992 | Japan. |
| 5-28634 | 4/1993 | Japan. |
| 7-533 | 6/1995 | Japan. |
| 7-289643 | 7/1995 | Japan. |
| 627828 | 10/1978 | U.S.S.R.. |
| 1 006 219 | 9/1965 | United Kingdom. |
| 1 419 702 | 12/1975 | United Kingdom. |
| 1 511 577 | 5/1978 | United Kingdom. |
| 2 180 454 | 1/1987 | United Kingdom. |
| 2 277 875 | 11/1994 | United Kingdom. |
| 2 272 159 | 11/1995 | United Kingdom. |
| WO84/04043 | 10/1984 | WIPO. |
| WO86/03129 | 6/1986 | WIPO. |
| WO88/00071 | 1/1988 | WIPO. |
| WO89/07958 | 9/1989 | WIPO. |
| WO91/05512 | 5/1991 | WIPO. |
| WO92/03178 | 3/1992 | WIPO. |
| WO92/11055 | 7/1992 | WIPO. |
| WO92/15356 | 9/1992 | WIPO. |
| WO92/19316 | 11/1992 | WIPO. |
| WO93/15786 | 8/1993 | WIPO. |
| WO93/20882 | 10/1993 | WIPO. |
| WO94/02194 | 2/1994 | WIPO. |
| WO94/11048 | 5/1994 | WIPO. |
| WO94/11053 | 5/1994 | WIPO. |
| WO94/14495 | 7/1994 | WIPO. |
| WO94/19039 | 9/1994 | WIPO. |
| WO94/23781 | 10/1994 | WIPO. |
| WO94/26174 | 11/1994 | WIPO. |
| WO95/02429 | 1/1995 | WIPO. |
| WO95/20992 | 8/1995 | WIPO. |
| WO95/28197 | 10/1995 | WIPO. |
| WO95/29730 | 11/1995 | WIPO. |
| WO96/04034 | 2/1996 | WIPO. |
| WO96/04036 | 2/1996 | WIPO. |
| WO96/04952 | 2/1996 | WIPO. |
| WO96/09848 | 4/1996 | WIPO. |
| WO96/10434 | 4/1996 | WIPO. |
| WO94/03229 | 2/1997 | WIPO. |

OTHER PUBLICATIONS

Cumberland, David C.; "Percutaneous Transluminal Angioplasty: A Review"; Clinical Radiology; vol. 34, No. 1, Jan. 1983; pp. 25–38.

Dotter, Charles T., MD; "Transluminal Angioplasty: A Long View", Diagnostic Radiology, Jun. 1980; pp. 561–564.

Earlam, Richard and J.R. Cunha–Melo; "Benign Oesophageal Strictures: Historical and Technical Aspects of Dilation"; The British Journal of Surgery; vol. 68, No. 12, Dec. 1981; pp. 829–836.

Fogarty, Thomas J.; "Adjunctive Intraoperative Arterial Dilation"; Archives of Surgery, vol. 116, Nov. 1981; pp. 1391–1397.

Fogarty, Thomas J.; "Combined Thrombectomy and Dilation for the Treatment of Acute Lower Extremity Arterial Thrombosis"; Journal of Vascular Surgery; vol. 10, No. 5, Nov. 1989; pp. 530–534.

Fogarty, Thomas J.; "Intraoperative Coronary Artery Balloon–Catheter Dilatation"; American Heart Journal; Apr. 1984; pp. 845–850.

Fogarty, Thomas J. et al.; "A Method for Extraction of Arterial Emboli and Thrombi"; Surgery, Gynecology & Obstetrics; Feb. 1963; pp. 241–244.

Fogarty, Thomas J., M.D.; "Management of Arterial Emboli"; Surgical Clinics of North America; vol. 59, No. 4, Aug. 1979; pp. 749–753.

Fogarty, Thomas J., MD and James C. Finn; "Peroperative Transluminal Angioplasty"; pp. 313–321.

Friedberg, Jacob, M.D.; "Dilation of Esophageal Strictures in Children, using a Fogarty Balloon Catheter"; Presented at the 33rd Annual Meeting of the Canadian Otolaryngological Society, Toronto, Jun. 1979.

Gruentzig, Andreas, MD and Bernhard Meier, MD; "Current Status of Dilatation Catheters and Guiding Systems"; The American Journal of Cardiology; vol. 53, Jun. 15, 1984; pp. 92C–93C.

Gruntzig, Andreas, M.D.; "PTCA Technique with a Double–Lumen Dilatation Catheter"; U.S. Department of Health; Proceedings of the Workshop on Percutaneous Transluminal Coronary Angioplasty; Jun. 15–16, 1979; pp. 123–133.

Gruntzig, Andreas; "Transluminal Dilatation of Coronary–Artery Stenosis"; The Lancet; Feb. 4, 1978; p. 263.

Hawkins, Jr., M.D. et al.; "Minicatheter and Deflector Technique for Renal Angioplasty"; Radiology; 145, Dec. 1982; pp. 837–838.

Kaltenback, M.; "The Long Wire Technique—a New Technique for Steerable Balloon Catheter Dilatation of Coronary Artery Stenosis"; European Heart Journal, 1984; pp. 1004–1009.

Kaltenback, M.; "New Technique for Steerable Balloon Dilatation of Coronary Artery Stenoses"; Zeitschrift für Kardiologie; 73, 1984; pp. 669–673.

Kugimiya, Toshisada et al.; "An Attempt at a Dilatation Method by Fogarty Balloon Catheter for Anastomotic Stricture resulting Postoperatively from Transection of the Esophagus"; 190th Nagasaki Surgical Symposium; Oct. 1970; pp. 1–13.

McAuley, Bruce J. MD et al.; "Advances in Guidewire Technology"; American Journal of Cardiology, 1984; pp. 94C–96C.

Moersch, Herman J., M.D.; "Cardiopasm: Its Diagnosis and Treatment"; The Division of Medicine of the Mayo Clinic; 1932; pp. 232–238.

Nordenstrom, Bjorn, M.D.; "Balloon Catheters for Percutaneous Insertion into the Vascular System"; The Department of Diagnostic Roentgenology; Sweeden; Mar. 2, 1962; pp. 411–416.

Nordenstrom, Bjorn, M.D.; "New Instruments for Catheterization and Angiocardiography"; *Radiology;* vol. 85; Jul.–Dec. 1965; pp. 256–259.

Nordenstrom, Bjorn; "Percutaneous Balloon–Occlusion of the Aorta: ACTA Radiologica"; vol. 4, Jan. 1966; pp. 365–374.

Nordenstrom, Bjorn; "Temporary Unilateral Occlusion of the Pulmonary Artery"; Stockholm, 1954; pp. 11–30.

Porstmann, W.; "A New Corset Balloon Catheter for Transluminal Recanalization According to Dotter with Special Consideration of Obliterations in Pelvic Arteries"; From the Department for Cardiovascular Diagnosis; pp. 239–244.

Seldinger, Sven Ivar; "Catheter Replacement of the Needle in Percutaneous Arteriography"; ACTA Radiologica, vol. 39; pp. 368–376.

Simpson, John B., PhD, MD et al.; "A New Catheter Sytem for Coronary Angioplasty"; The American Journal of Cardiology, vol. 49, Apr. 1, 1982; pp. 1216–1222.

Turnquist, Carl R.; "Balloon Catheters and Transluminal Dilatation: Technical Considerations", AJR 135, Nov. 1980; pp. 901–906.

Waltman, Arthur C., M.D.; "Transluminal Angioplasty: General Rules and Basic Consdierations"; Interventional Radiology; W.B. Saunders Company, 1982; pp. 253–272.

Zeitler, Eberhard, M.D.; "Results of Percutaneous Transluminal Angioplasty"; Radiology; Jan. 1983; pp. 57–60.

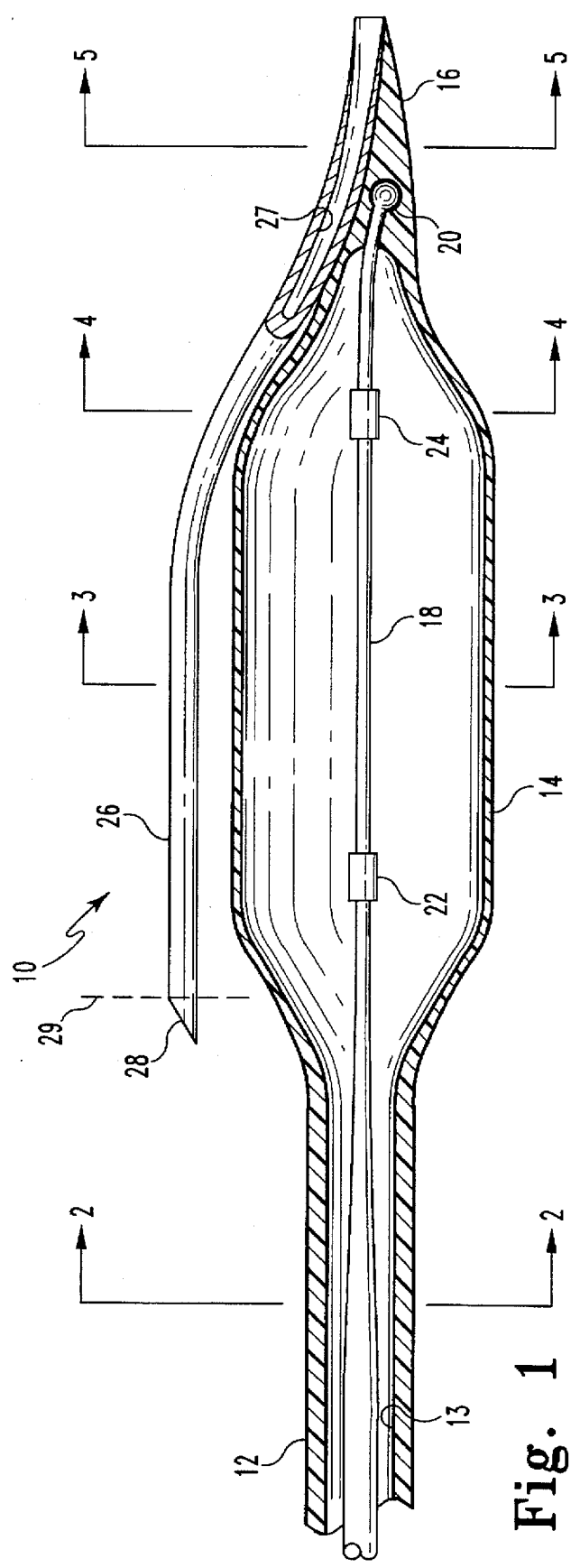

RAPID EXCHANGE STENT DELIVERY BALLOON CATHETER

TECHNICAL FIELD OF THE INVENTION

The present invention generally relates to balloon catheters and, more particularly, to a rapid exchange stent delivery balloon catheter.

BACKGROUND OF THE INVENTION

The use of balloon catheters to treat strictures, stenoses, or narrowings within various parts of the human body is well known. In a typical procedure, for example to dilate a stenosis in the coronary arteries, a relatively large guiding catheter is inserted into the patient's arterial system in the groin. The guiding catheter is then advanced through the arteries to a location near the patient's heart. A small wire guide is then inserted into the guiding catheter and advanced to the distal end of the guiding catheter, at which point it is steered to extend through the stenosis in the coronary arteries. A balloon catheter is then advanced over the wire guide until the deflated balloon lies across the stenosis. A working fluid is then pumped through the balloon catheter, thereby inflating the balloon and dilating the passage through the stenosis.

After such a dilitation procedure, it is often found desirable to install a stent in the area of the stenosis in order to ensure patency of the lumen in the artery. Such a stent is delivered on the end of an inflatable balloon stent delivery catheter. The deformable stent is wrapped around the deflated balloon of the catheter and the catheter is inserted into the patient's body to the location of the stenosis. When the balloon of the stent delivery catheter is inflated, the stent is plastically deformed to an expanded condition, the balloon is deflated, and the stent delivery catheter is withdrawn, leaving the expanded stent in place to preserve the patency of the arterial lumen. Because such stent delivery catheters have wire guide lumens which extend the entire length of the catheter, they cannot be inserted to the stenosis site over the wire guide which is used to insert the balloon angioplasty catheter (such wire guides are too short). Therefore, after the stenosis has been dilated, the balloon angioplasty catheter and wire guide are removed from the guiding catheter and a second wire guide, or exchange wire guide, is inserted through the guiding catheter and steered to the stenosis location. The exchange wire guide is more than twice as long as the stent delivery catheter because it is necessary that the wire guide protrude from the patient's body by a length greater than the length of the stent delivery catheter. This allows the exchange wire guide to be held steady with the physician's hand while the stent delivery catheter is advanced over the exchange wire guide. Once the distal end of the stent delivery catheter has been placed within the area of the dilated stenosis, the balloon of the stent delivery catheter may be inflated, thereby plastically deforming the stent in the region of the dilated stenosis. The balloon of the stent delivery catheter is then deflated, allowing the stent delivery catheter to be withdrawn, leaving the expanded stent in place. The exchange wire guide and the guiding catheter are then withdrawn, thereby completing the operation.

In situations where physicians find it desirable to install a stent after the balloon angioplasty procedure, the need to replace the wire guide with an exchange wire guide is a cumbersome and undesirable requirement. This is due to the fact that it is necessary that the second exchange wire guide be steered through the patient's arterial system until it reaches the location of the original stenosis. Furthermore, the great length of the exchange wire guide which extends outside of the patient's body must sometimes extend beyond the sterile area of the surgical table.

There is therefore a need in the prior art for a stent delivery catheter which may be used with the same wire guide that is used to steer the balloon angioplasty catheter. The present invention is directed toward meeting this need.

SUMMARY OF THE INVENTION

The present invention relates to a rapid exchange stent delivery balloon catheter which allows exchange from a balloon angioplasty catheter to a stent delivery catheter without the need to replace the angioplasty catheter wire guide with an exchange-length wire guide before exchanging the catheters. The stent delivery catheter of the present invention includes a relatively short wire guide shaft which is bonded to the catheter shaft only at a location distal to the inflation lumen.

In one form of the invention, a rapid exchange stent delivery balloon catheter is disclosed, comprising a catheter shaft defining an inflation lumen, the inflation lumen having a proximal end and a distal end; an inflatable balloon having a proximal end and a distal end; a wire guide shaft defining a wire guide lumen, the wire guide shaft having a proximal end and a distal end; and a catheter tip having a proximal end and a distal end; wherein the distal end of the inflation lumen opens into and is in fluid communication with an interior of the inflatable balloon, the distal end of the inflatable balloon is sealed by the proximal end of the catheter tip, and the wire guide shaft is coupled to the catheter tip, said coupling being completely distal of the distal end of the inflatable balloon.

In another form of the invention, a balloon catheter stent configuration is disclosed comprising a catheter shaft defining an inflation lumen having a proximal end and a distal end; an inflatable balloon having a proximal end and a distal end; a wire guide shaft defining a wire guide lumen, said wire guide shaft having a proximal end and a distal end; a catheter tip having a proximal end and a distal end; and a stent mounted on and surrounding said inflatable balloon and wire guide shaft; wherein the distal end of the inflation lumen opens into and is in fluid communication with the inflatable balloon, the distal end of the inflatable balloon is sealed by the proximal end of the catheter tip, and the wire guide shaft is coupled to the catheter tip, said coupling being completely distal of the distal end of the inflatable balloon.

BRIEF DESCRIPTION OF THE DRAWINGS

FIG. 1 is a partial cross-sectional side view of a first embodiment rapid exchange stent delivery balloon catheter of the present invention.

FIG. 2 is a first cross-sectional view of the catheter of FIG. 1 taken along the section line 2—2.

FIG. 3 is a second cross-sectional view of the catheter of FIG. 1 taken along the section line 3—3.

FIG. 4 is a third cross-sectional view of the catheter of FIG. 1 taken along the section line 4—4.

FIG. 5 is a fourth cross-sectional view of the catheter of FIG. 1 taken along the section line 5—5.

DETAILED DESCRIPTION OF THE PREFERRED EMBODIMENTS

Figure 6A:
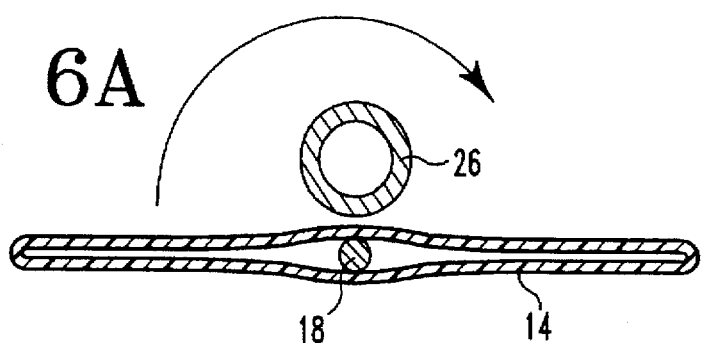
FIGS. 6A–C are cross-sectional views of a folding procedure for the catheter of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a preferred embodiment of the present invention is illustrated in a partial cross-sectional side view with the balloon inflated, and indicated generally at 10. The catheter 10 includes a catheter shaft 12 defining an inflation lumen 13 which extends far enough in the proximal direction (not shown) in order to allow the proximal end of the catheter 10 to be outside of the patient's body when the inflatable balloon is placed across the stenosis. Near the distal end of the catheter 10, the inflation lumen 13 opens into the interior of an inflatable balloon 14. The distal end of the inflatable balloon 14 is closed and merges into a catheter tip 16. A stiffening wire 18 extends through the inflation lumen 13 and the interior of the inflatable balloon 14 and terminates within the catheter tip 16. The stiffening wire 18 preferably includes a small ball or other enlargement 20 at its distal end in order to anchor the stiffening wire 18 within the catheter tip 16. The stiffening wire is preferably formed from stainless steel or any other suitable stiff material. Alternatively, the stiffening wire may be made from nitinol in the superelastic condition, which would have the advantage of making the catheter 10 kink resistant. A radiopaque marker band 22 is placed around the stiffening wire 18 near the proximal end of the inflatable balloon 14, while a second radiopaque marker band 24 is placed around the stiffening wire 18 near the distal end of the inflatable balloon 14. For the purposes of the present disclosure, the ends of the inflatable balloon 14 are defined as the regions where the balloon 14 begins to taper away from its maximum radial dimension. The radiopaque marker bands 22 and 24 may be made of any radiopaque material, such as gold, tungsten, or silver. The location of the radiopaque marker bands 22 and 24 near the proximal and distal ends of the inflatable balloons 14 allow the position of the inflatable balloon 14 to be accurately determined by flouroscopy in order to ensure proper positioning of the inflatable balloon 14 prior to inflation.

The stent delivery catheter 10 further includes a tubular wire guide shaft 26 including and defining a wire guide lumen 27 which is bonded to the rest of the catheter 10 only in the region of the catheter tip 16. The wire guide shaft 26 includes open distal and proximal ends in order to allow a wire guide to pass therethrough. The proximal end 28 of the wire guide shaft 26 is preferably cut at an angle to the transverse axis of the wire guide shaft 26. This reduces the chance of damage to the vessel wall as the catheter 10 is withdrawn. If the proximal end 28 of the wire guide shaft 26 were cut transverse to the axis of the wire guide shaft 26, such a blunt edge would be prone to damage the vessel wall as the catheter 10 is withdrawn. The proximal end of the catheter tube 12 preferably terminates with a standard female luer type fitting (not shown) for attachment to a syringe for inflation and deflation of the inflatable balloon 14.

The stent delivery catheter 10 is preferably formed from radiation cross-linked polyethylene. Stents of various types are able to grip a folded polyethylene balloon well, such balloons have fairly good strength, and catheters and balloons formed from polyethylene have good flexibility. It would also be possible to form the catheter 10 from other materials such as nylons and PET.

Referring now to FIG. 2, a cross-sectional view of the stent delivery catheter is illustrated, taken along section line 2—2. The stiffening wire 18 is visible within the lumen 13 of the catheter shaft 12. FIG. 3 is a second cross-sectional view of the catheter 10, taken along section line 3—3. The stiffening wire 18 is visible within the expanded balloon 14, and the wire guide shaft 26 is exterior to the inflatable balloon 14 and not bonded thereto. FIG. 4 is a third cross-sectional view of the catheter 10, taken along section line 4—4. The stiffening wire 18, surrounded by the radiopaque marker band 24, is visible within the inflatable balloon 14. The wire guide shaft 26 is separate from the inflatable balloon 14 and not attached thereto. FIG. 5 is a fourth cross-sectional view of the catheter 10, taken along section line 5—5. At this point, the wire guide shaft 26 has been merged within the tip 16 of the catheter 10. In a preferred embodiment of the present invention, the proximal end 28 of the wire guide shaft 26 extends to approximately the proximal end of the transition between the catheter shaft 12 and the inflatable balloon 14. However, those skilled in the art will recognize that it is possible to form the wire guide shaft 26 such that the proximal end 28 lies between the proximal and distal ends of the inflation balloon 14. Furthermore, the wire guide shaft 26 may be formed to lie completely distal of the inflatable balloon 14. The required length of the wire guide shaft 26 is dependent upon the overall length of the stent delivery catheter 10 and the number and severity of the tortuous vessel turns which must be executed by the catheter 10. Generally, the longer the wire guide shaft 26, the greater the trackability of the catheter 10.

Figure 6B:
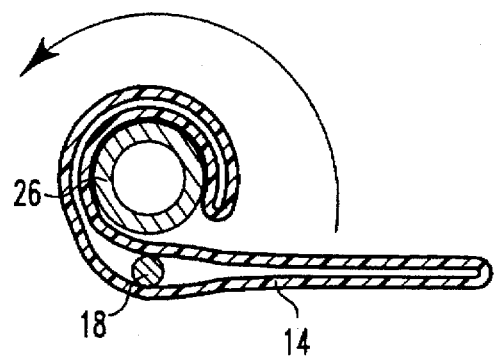
Figure 6C:
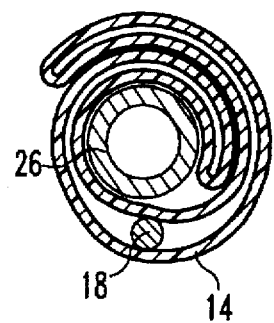
Figure 6D:
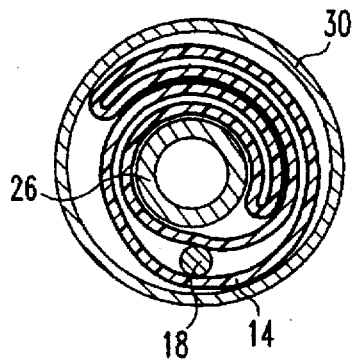
FIG. 6D is a cross-sectional view of the folded catheter of FIG. 1 with a stent installed thereupon.

Referring now to FIGS. 6A-C, the stent delivery catheter 10 is illustrated in cross-sectional view along the same section line used for FIG. 3. The balloon 14 is shown in its deflated and flattened condition. In FIG. 6A, one-half of the deflated balloon 14 is folded over the top of the wire guide shaft 26. In FIG. 6B, the other half of the deflated balloon 14 is folded over the top of the wire guide shaft 26, thereby sandwiching the first half of the inflated balloon 14 between the second half of the deflated balloon 14 and the wire guide shaft 26. Once the balloon has been folded around the wire guide shaft 26, it has a relatively small cross-sectional diameter. As illustrated in FIG. 6D, a deformable stent 30 may be placed around the folded catheter 10. The stent 30 will typically be placed around the catheter 10 in a radially contracted configuration such that the stent 30 securely hugs the folded balloon 14, thereby preventing the stent 30 from dislodging from the catheter 10 during insertion. Once the catheter 10/stent 30 have been positioned across the dilated stenosis, the balloon 14 may be inflated by injecting working fluid through the inflation lumen 13. Expansion of the balloon 14 causes radial expansion of the stent 30 until the inside diameter of the expanded stent 30 is equal to or greater than the outside diameter of the inflated balloon 14. Because the stent 30 is plastically deformed during radial expansion, it retains it's expanded diameter when the balloon 14 is deflated by evacuation of the working fluid through the inflation lumen 13. At this point, the stent delivery catheter 10 may be withdrawn, leaving the expanded stent 30 in the area of the stenosis in order to maintain patency of the vessel. The stent delivery catheter 10 of the present invention may be used with any balloon expandable stent design.

The stent delivery catheter 10 of the present invention can be used to place balloon expanded stents in several parts of the anatomy, and is not limited solely to placement of stents in the coronary arteries. For use in coronary arteries, the balloon 14 diameter should have a range of approximately 2.0–5.0 mm. The balloon length should be approximately 15–45 mm. The inside diameter of the wire guide shaft 26 (i.e. the diameter of the lumen 27) should be approximately 0.5 mm. The overall length of the catheter 10 should be approximately 110–180 cm. The stiffening wire should be approximately 0.010–0.015 inches in diameter. The distal end of the stiffening wire can be tapered in order to allow more flexibility at the distal end of the catheter 10. The distal section of the stiffening wire should be approximately 0.008–0.012 inches in diameter for a length of approximately 3–15 cm. proximal of the distal tip 20, at which point the stiffening wire 18 should taper up to a full stiffening wire diameter for a length of approximately 2–10 cm. The outside diameter of the catheter shaft 12 should be approximately 1–1.5 mm.

For peripheral vessels, bile ducts and other parts of the anatomy, the balloon 14 diameter should range from 5–15 mm., the balloon 14 length should be approximately 15–60 mm., the catheter shaft 12 should range up to 3.5 mm. outside diameter, and the inside diameter of the wire guide shaft 26 should go up to approximately 1.5 mm.

The stent delivery catheter 10 is preferably formed by starting with a length of tubing which is equal in cross-sectional dimensions to the desired dimensions of the catheter shaft 12. The distal end of this tubing is closed and a portion of the tubing is placed into a mold which has the shape and dimensions of the desired size of the inflated balloon 14. The section of the tubing within the mold is then heated and the interior of the tubing is pressurized such that the portion of the tubing within the mold expands to the interior dimensions of the mold. The tubing is then cooled such that the material within the mold retains the shape of the interior of the mold. The mold is then removed and the distal end of the tubing is cut distal to the distal end of the balloon at the desired distance.

A second section of tubing having dimensions desired for the wire guide shaft 26 is then placed next to the balloon 14 such that the distal end of the wire guide shaft 26 is adjacent the distal end of the tubing. A wire mandrel is then inserted into the wire guide lumen 27 until the distal end of the wire mandrel is adjacent the distal end of the wire guide lumen 27. The distal ends of the wire guide shaft 26 and the tubing are then inserted into a mold which has an interior shape and dimensions which match the distal end of the catheter 10 as illustrated in FIG. 1. The plastic within this mold is then heated to above the melting temperature of the plastic material in order to bond the wire guide shaft 26 to the newly formed catheter tip 16. The mandrel within the wire guide lumen 27 maintains the patency of this lumen. At the same time that the wire guide shaft 26 is being bonded to the catheter tip 16, the stiffening wire 18 is inserted through the lumen 13 and the balloon 14 such that the tip 20 extends into the molten plastic material. The end of the catheter shaft is then cooled to below the melting point of the plastic material, thereby solidifying the stiffening wire tip 20 within the distal tip 16 of the catheter and bonding the wire guide shaft 26 to the distal end 16. The mandrel is then removed from the wire guide lumen and construction of the catheter is complete.

The stent delivery catheter 10 of the present invention has the advantage that it allows the exchange from the balloon angioplasty catheter to the stent delivery catheter without the need to replace the wire guide with an exchange-length wire guide before exchanging the catheters. The wire guide is simply left undisturbed, the angioplasty catheter is removed and the stent delivery catheter is introduced. The short wire guide shaft 26 allows the operator to maintain control of the wire guide while introducing the stent delivery catheter 10. Having the wire guide shaft 26 extend from the distal end to the proximal end of the balloon 14 allows the wire guide and wire guide shaft 26 to be threaded through the interior of the stent 30 so that the wire guide and wire guide shaft 26 are inside the stent 30 when the stent 30 is expanded, and not trapped between the stent 30 and the vessel wall.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A rapid exchange stent delivery balloon catheter, comprising:

a catheter shaft defining an inflation lumen, the inflation lumen having a proximal end and a distal end;

an inflatable balloon having a proximal end and a distal end;

a wire guide shaft defining a wire guide lumen, the wire guide shaft having a proximal end and a distal end, wherein the proximal end of the wire guide shaft is proximal to the proximal end of the inflatable balloon; and a catheter tip having a proximal end and a distal end;

wherein the distal end of the inflation lumen opens into and is in fluid communication with an interior of the inflatable balloon, the distal end of the inflatable balloon is sealed by the proximal end of the catheter tip, and the wire guide shaft is coupled only to the catheter tip completely distally of the distal end of the inflatable balloon.

2. The stent delivery balloon catheter of claim 1, wherein the distal end of the wire guide shaft is adjacent the distal end of the catheter tip.

3. The stent delivery balloon catheter of claim 1, wherein the proximal end of the wire guide shaft is formed at an angle to a transverse axis of the wire guide shaft.

4. The stent delivery balloon catheter of claim 1, further comprising:

a stiffening wire having a proximal end and a distal end;

wherein the stiffening wire extends through the interior of the inflatable balloon.

5. The stent delivery balloon catheter of claim 4, wherein the distal end of the stiffening wire is coupled to the catheter tip.

6. The stent delivery balloon catheter of claim 5, further comprising a spherical ball coupled to the distal end of the stiffening wire.

7. The stent delivery balloon catheter of claim 4, further comprising: at least one radiopaque marker band coupled to the stiffening wire.

8. The stent delivery balloon catheter of claim 7, wherein the at least one radiopaque marker band marks a location of at least one end of the inflatable balloon.

9. The stent delivery balloon catheter of claim 7, wherein the at least one radiopaque marker band is formed from gold.

10. The stent delivery balloon catheter of claim 4, wherein the stiffening wire is formed from stainless steel.

11. The stent delivery balloon catheter of claim 1, wherein the inflatable balloon is folded around the wire guide shaft.

12. The stent delivery balloon catheter of claim 11, further comprising:

an expandable stent disposed around the folded inflatable balloon.

13. The stent delivery balloon catheter of claim 1, wherein the catheter shaft, the inflatable balloon, the wire guide shaft and the catheter tip are formed from radiation cross-linked polyethylene.

14. A balloon catheter stent configuration comprising:
 a catheter shaft defining an inflation lumen having a proximal end and a distal end;
 an inflatable balloon having a proximal end and a distal end;
 a wire guide shaft defining a wire guide lumen, said wire guide shaft having a proximal end and a distal end, wherein the proximal end of the wire guide shaft is proximal to the proximal end of the inflatable balloon;
 a catheter tip having a proximal end and a distal end; and
 a stent mounted on and surrounding said inflatable balloon and wire guide shaft;
 wherein the distal end of the inflation lumen opens into and is in fluid communication with the inflatable balloon, the distal end of the inflatable balloon is sealed by the proximal end of the catheter tip, and the wire guide shaft is coupled only to the catheter tip completely distally of the distal end of the inflatable balloon.

* * * * *